(12) United States Patent
Pak et al.

(10) Patent No.: US 7,910,518 B2
(45) Date of Patent: Mar. 22, 2011

(54) GEOMETRICALLY SIZED SOLID SHAPED CARRIER FOR OLEFIN EPOXIDATION CATALYST

(75) Inventors: Serguei Pak, Teaneck, NJ (US); Andrzej Rokicki, Mountain Lakes, NJ (US); Howard Sachs, Bronx, NY (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 100 days.

(21) Appl. No.: 12/045,251

(22) Filed: Mar. 10, 2008

(65) Prior Publication Data
US 2009/0227820 A1 Sep. 10, 2009

(51) Int. Cl.
- B01J 23/00 (2006.01)
- B01J 21/00 (2006.01)
- B01J 20/00 (2006.01)
- B01J 29/00 (2006.01)
- B01J 31/00 (2006.01)

(52) U.S. Cl. ............ 502/347; 502/60; 502/63; 502/64; 502/66; 502/74; 502/87; 502/240; 502/243; 502/258; 502/261; 502/262; 502/263; 502/300; 502/305; 502/306; 502/308; 502/309; 502/313; 502/314; 502/317; 502/319; 502/320; 502/323; 502/330; 502/332; 502/333; 502/334; 502/335; 502/336; 502/337; 502/338; 502/339; 502/348; 502/349; 502/350; 502/355; 502/407; 502/415; 502/439; 502/527.19

(58) Field of Classification Search .............. 502/60, 502/63, 64, 66, 74, 87, 88, 240, 243, 258, 502/261, 262, 263, 300, 305, 306, 308, 309, 502/313, 314, 317, 319, 320, 323, 330, 332, 502/333, 334, 335, 336, 337, 338, 339, 349, 502/350, 355, 407, 415, 439, 527.19; 422/170–180
See application file for complete search history.

(56) References Cited

U.S. PATENT DOCUMENTS

| | | | |
|---|---|---|---|
| 2,950,169 A | 8/1960 | Murray et al. | |
| 3,172,866 A | 3/1965 | Belon | |
| 3,222,129 A | 12/1965 | Osment et al. | |
| 3,331,787 A * | 7/1967 | Bair et al. | 502/223 |
| 3,397,154 A * | 8/1968 | Talsma | 502/304 |
| 3,489,809 A * | 1/1970 | Romeo, Sr. et al. | 585/260 |
| 3,563,914 A | 2/1971 | Wattimena | |
| 3,702,259 A | 11/1972 | Nielsen | |
| 4,226,782 A | 10/1980 | Hayden et al. | |
| 4,242,235 A | 12/1980 | Cognion et al. | |
| 4,260,524 A * | 4/1981 | Yamada et al. | 502/439 |
| 4,335,023 A * | 6/1982 | Dettling et al. | 502/262 |
| 4,460,704 A * | 7/1984 | Twigg | 502/302 |
| 4,761,394 A | 8/1988 | Lauritzen | |
| 4,766,105 A | 8/1988 | Lauritzen | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,112,795 A | 5/1992 | Minahan et al. | |
| 5,187,140 A | 2/1993 | Thorsteinson et al. | |
| 5,266,548 A | 11/1993 | Koradia et al. | |
| 5,380,697 A | 1/1995 | Matusz et al. | |
| 5,407,888 A | 4/1995 | Herzog et al. | |
| 5,597,773 A | 1/1997 | Evans et al. | |
| 5,831,037 A | 11/1998 | Ohsuga et al. | |
| 6,541,407 B2 * | 4/2003 | Beall et al. | 501/119 |
| 6,624,114 B1 * | 9/2003 | Eberle et al. | 502/439 |
| 6,831,037 B2 | 12/2004 | Szymanski et al. | |
| 6,864,198 B2 * | 3/2005 | Merkel | 501/80 |
| RE38,888 E * | 11/2005 | Beall et al. | 501/119 |
| 6,967,186 B2 * | 11/2005 | Takaya et al. | 502/325 |
| 7,183,236 B2 * | 2/2007 | Hase et al. | 502/439 |
| 7,307,039 B2 * | 12/2007 | Iwakuni et al. | 502/304 |
| 7,520,911 B2 * | 4/2009 | Beall et al. | 55/523 |
| 7,553,349 B2 * | 6/2009 | Gadkaree et al. | 55/523 |
| 7,589,046 B2 * | 9/2009 | Dieterle et al. | 502/311 |
| 7,601,671 B2 * | 10/2009 | LaBarge | 502/326 |
| 7,704,296 B2 * | 4/2010 | Merkel | 55/523 |
| 7,740,819 B2 * | 6/2010 | Morita et al. | 423/247 |
| 7,744,980 B2 * | 6/2010 | Boorom et al. | 428/116 |
| 2001/0038812 A1 * | 11/2001 | Yavuz et al. | 423/213.2 |
| 2001/0043896 A1 * | 11/2001 | Domesle et al. | 423/213.5 |
| 2003/0162650 A1 * | 8/2003 | Marques et al. | 502/64 |
| 2003/0171217 A1 * | 9/2003 | Koike et al. | 502/439 |
| 2003/0176280 A1 * | 9/2003 | Caze et al. | 502/439 |

(Continued)

FOREIGN PATENT DOCUMENTS

| | | |
|---|---|---|
| EP | 0229465 B2 | 6/1995 |
| EP | 0218766 B2 | 7/1995 |

OTHER PUBLICATIONS

Brunauer, S. et al., "Adsorption of Gases in Multimolecular Layers," E., J. Am. Chem. Soc., 60, 309-16 (1938). Drake, L.C., et al., "Macropore-Size Distributions in Some Typical Porous Substances," Ind. Eng. Chem. Anal. Ed., 17, 787 (1945).
Perry, R.H. et al., "Perry's Chemical Engineers' Handbook," Sixth Edition, McGraw-Hill, 1984, p. 4-40.

*Primary Examiner* — Cam N Nguyen

(74) *Attorney, Agent, or Firm* — Scully, Scott, Murphy & Presser, P.C.

(57) ABSTRACT

A geometrically shaped solid carrier is provided that improves the performance and effectiveness of an olefin epoxidation catalyst for epoxidizing an olefin to an olefin oxide. In particular, improved performance and effectiveness of an olefin epoxidation catalyst is achieved by utilizing a geometrically shaped refractory solid carrier in which at least one wall thickness of said carrier is less than 2.5 mm.

23 Claims, No Drawings

U.S. PATENT DOCUMENTS

| | | | |
|---|---|---|---|
| 2003/0224933 A1* | 12/2003 | Kondo et al. | 502/439 |
| 2004/0110973 A1 | 6/2004 | Matusz | |
| 2004/0225138 A1 | 11/2004 | McAllister et al. | |
| 2004/0260103 A1 | 12/2004 | Matusz et al. | |
| 2005/0096219 A1 | 5/2005 | Szymanski et al. | |
| 2005/0227869 A1* | 10/2005 | Ohno et al. | 502/439 |
| 2005/0266992 A1* | 12/2005 | Ohno et al. | 502/439 |
| 2006/0178265 A1* | 8/2006 | Kita et al. | 502/439 |
| 2006/0252643 A1 | 11/2006 | Pak | |
| 2007/0054803 A1* | 3/2007 | Miyairi | 502/439 |
| 2007/0173403 A1* | 7/2007 | Koike et al. | 502/300 |
| 2008/0070776 A1* | 3/2008 | Yamaguchi | 502/100 |
| 2008/0125316 A1* | 5/2008 | Noda et al. | 502/439 |

* cited by examiner

US 7,910,518 B2

GEOMETRICALLY SIZED SOLID SHAPED CARRIER FOR OLEFIN EPOXIDATION CATALYST

FIELD OF THE INVENTION

The present invention relates to a carrier useful as a component of a catalyst, particularly as a component of an epoxidation catalyst. More specifically, the present invention relates to a geometrically sized solid shaped carrier, an epoxidation catalyst including the geometrically sized solid shaped carrier and a process of epoxiding an olefin utilizing the inventive epoxidation catalyst.

BACKGROUND OF THE INVENTION

In olefin epoxidation, an olefin is reacted with oxygen to form an olefin epoxide using a catalyst comprising a silver component, usually with one or more elements deposited on a carrier. Catalyst performance is characterized on the basis of selectivity, activity and stability. Moreover, the performance in the reactor tubes is characterized by the packing density of the catalyst in the volume of the tubes and pressure drop.

The selectivity is the molar fraction of the converted olefin yielding the desired olefin oxide. Quite modest improvements in selectivity and the maintenance of selectivity over longer time yield huge dividends in terms of process efficiency.

Packing of the catalyst in the reactor tube depends on the geometrical size and shape of the carrier that the catalyst is deposited on. Typically higher packing density, i.e., more catalyst in the volume, is considered as advantageous.

Alumina is well known to be useful as a carrier for olefin epoxidation catalysts. Carrier materials including alumina are typically made by fusing high purity aluminum oxide with or without silica. For this purpose, the carrier material often comprises 90 percent or more by weight alpha alumina, and 1 to 6 percent by weight silica. The carrier may be very porous or non-porous and have a high or low surface area depending upon the intended use of the carrier. The carrier may contain any porous material that does not detrimentally influence the catalytic reaction where it is used.

In the process of making a carrier, high-purity aluminum oxide, preferably alpha alumina, is thoroughly mixed with temporary and permanent binders. The temporary binders are thermally decomposable organic compounds of moderate to high molecular weight which, on decomposition, produce the desired pore structure of the carrier. The permanent binders are inorganic clay-type materials having fusion temperatures below that of the alumina and impart mechanical strength to the finished carrier. After thorough dry-mixing, sufficient water or another solvent is added to the mass to form the mass into a paste-like substance. The carrier particles for making the catalyst are formed from the paste by conventional means such as, for example, high pressure extrusion, granulation or other ceramic forming processes. The particles are then dried and are subsequently fired at an elevated temperature.

In the firing step, the temporary binders are thermally decomposed and are volatilized, leaving voids in the carrier mass. These voids are the genesis of the pore structure of the finished carrier. As firing continues, the temperature reaches the point at which the permanent binder turns into inorganic clay. The catalyst carrier is then cooled, and during cooling the permanent binder sets, acting to bond the carrier particles, and thereby impart mechanical strength to the carrier and ensure maintenance of the pore structure.

Catalyst carriers of desired characteristics can be readily produced by the foregoing procedure. Pore size, pore distribution and porosity are readily controlled by appropriate adjustment of the size of the starting alumina particles, and of the particle size and concentration of the temporary and/or the permanent binders in the mixture. The larger the starting alumina particle size, the greater the porosity of the finished catalyst. The more homogenous in size are the alumina particles, the more uniform the pore structure. Similarly, increasing the concentration of the temporary binder also increases the overall porosity of the finished catalyst carrier.

The preparation of alumina carriers of particular physical properties and porous structure for ethylene epoxidation catalyst performance enhancement are described, for example, in U.S. Pat. Nos. 4,226,782, 4,242,235, 5,266,548, 5,380,697, 5,597,773, 5,831,037 and 6,831,037 as well as in U.S. Patent Application Publication Nos. 2004/0110973 A1 and 2005/0096219 A1.

In addition to the preparation of alumina carriers, the prior art also describes the preparation of alumina shaped carriers for catalytic applications in various shapes for different purposes. For example, U.S. Pat. No. 2,950,169 describes a method of preparing pills of high crushing strength. For many uses, it is preferred that the alumina be in particles of uniform size and shape, including, for example, cylindrical pills, spheres, polyhedra, tubular cylindrical pills, etc.

U.S. Pat. No. 3,222,129 relates to an active alumina product which has improved resistance to attrition, abrasion and crushing. Alumina may be manufactured in shaped nodules or pellets, etc., in the forms of spheres, or the like, preferably of uniform size and shape. The shaped nodules are particularly desirable because they can be more easily handled than granular or particulate material.

Alumina carriers for ethylene epoxidation in various shapes, such as balls, granules, rings or the like, as described, for example, in U.S. Pat. No. 3,172,866 are known, however, little is known about the shape and performance relation. Among such examples are U.S. Patent Application Publication Nos. 2004/0260103 A1 and U.S. 2004/0225138 A1 which describe a catalyst and reactor system for the manufacture of ethylene oxide. This prior art catalyst was made on a carrier of a particular geometrical configuration. A proper selection of geometrical size of a hollow cylinder reportedly increased the packing density at acceptable pressure drop values in the reactor. It was specifically identified that an advantageous support material has a hollow cylinder geometric configuration defined by a ratio of nominal outside diameter-to-nominal inside diameter. The smaller than conventional bore diameter helps provides for an improvement in the average crush strength of the agglomerate, and provides for packing a greater amount of support material into same volume, allowing for more silver to be loaded into the same volume.

As described above, a catalyst for ethylene epoxidation requires a carrier with specific physical properties and those carriers can be shaped in various shapes of different sizes. The carrier properties and shape are important for loading catalytically active silver in the reactor tubes. It would be desirable to improve performance and effectiveness of a catalyst used in the reactor tubes by improvements in physical properties and geometrical shape of the carrier.

SUMMARY OF THE INVENTION

The invention provides a geometrically sized solid shaped carrier for a catalyst particularly useful for a catalyst employed in the epoxidation of an olefin. Specifically, the invention provides a refractory solid carrier that is shaped into various geometric forms having thin walls. The term "thin walls" is used in the present invention to denote the wall thickness between opposing walls of a particular geometric shape (e.g., inner and outer wall surfaces of a hollow cylinder) is preferably less than 2.5 mm, more preferably less than 2.0 mm, and even more preferably less than 1.5 mm.

The geometrically sized shaped solid carrier provided in the present invention may be in the form of hollow cylinders, three-holes, wagon wheels, cross-partitioned hollow cylinders, honeycombs and etc. Each of the geometric shapes would have thin walls as defined above.

Moreover, the invention provides specific values of geometrically sized solid shaped carrier wall thickness that improves performance and effectiveness of a catalyst used in a reactor. Specifically, and when the carrier is shaped as a hollow cylinder, with a wall thickness less than 2.5 mm, the carrier makes the catalyst function more effectively at a reduced pressure drop, and reduces the amount of catalyst and materials used in its preparation, such materials being silver and promoters.

In one aspect, the present invention provides a carrier for a catalytic system including at least one catalytically active metal disposed thereon comprising:

a geometrically shaped refractory solid carrier in which at least one wall thickness of said geometrically shaped refractory solid carrier is less than 2.5 mm.

In one embodiment of the invention, the inventive carrier has a geometric shape in which all of the walls are thin, i.e., less than 2.5 mm.

In another embodiment of the invention, the inventive carrier has a total pore volume (PV) from about 0.2 ml/g to about 0.6 ml/g and optionally at least one of the following additional characteristics: (i) a surface area from about 0.3 to about 3.0 $m^2/g$; preferably from about 0.6 to about 2.5 $m^2/g$; and most preferably from about 0.9 to about 2.0 m/g; (ii) at least 40% of the PV from pores with diameters between 1 and 5 micrometers; preferably at least 60%; and most preferably at least 80%; (iii) a pore size distribution between 1 and 5 micrometers; preferably between 1 and 4.5 micrometers; and most preferably between 1 and 4 micrometers; (iv) a pore volume from pores with a diameter of 5 micrometers and above less than 0.20 ml/g; preferably less than 0.10 ml/g; and most preferably less than 0.05 ml/g; and (v) a pore volume from pores with a diameter smaller than 1 micrometer less than 0.20 ml/g; preferably less than 0.16 ml/g; and most preferably less than 0.12 ml/g.

In a further embodiment of the present invention, the inventive carrier includes hollow cylinders, three-holes, wagon wheels, cross-partitioned hollow cylinders, and honeycombs having the above mentioned wall thickness.

In yet a further embodiment of the present invention, a carrier is provided that comprises a geometrically shaped refractory solid carrier in which at least one wall thickness of said geometrically shaped refractory solid carrier is less than 2.5 mm, said carrier comprises aluminum oxide having a total pore volume from about 0.2 ml/g to about 0.6 ml/g, a surface area from about 0.3 to about 3.0 $m^2/g$, at least 40% of the pore volume from pores with diameters between 1 and 5 micrometers, a pore size distribution between 1 and 5 micrometers, a pore volume from pores with a diameter of 5 micrometers and above less than 0.20 ml/g, and a pore volume from pores with a diameter smaller than 1 micrometer less than 0.20 ml/g.

In another aspect of the invention, a catalyst useful for the epoxidation of an olefin is provided that comprises a geometrically shaped refractory solid carrier in which at least one wall thickness of said carrier is less than 2.5 mm and a catalytically effective amount of silver disposed thereon.

In some embodiments, the inventive catalyst further comprises a promoting amount of a promoter thereon. In this embodiment of the invention, the promoter comprising one or more of an alkali metal containing compounds, one or more transition metal containing compounds, one or more sulfur components, one or more fluorine containing components, or combinations thereof.

In a further embodiment of the inventive catalyst, the promoter is a transition metal comprising an element selected from Groups VB, VIIB, VIIB and VIII of the Periodic Table of the Elements, and combinations thereof. In a preferred embodiment, the transition metal comprises rhenium, molybdenum, tungsten or combinations thereof.

In a yet further embodiment of the inventive catalyst, the promoter is an alkali metal containing compound comprising lithium, sodium, potassium, rubidium, cesium or combinations thereof.

In a preferred embodiment of the invention, the inventive catalyst comprises a geometrically shaped refractory solid carrier in which at least one wall thickness of said geometrically shaped refractory solid carrier is less than 2.5 mm, said carrier comprises aluminum oxide having a total pore volume from about 0.2 ml/g to about 0.6 ml/g, a surface area from about 0.3 to about 3.0 $m^2/g$, at least 40% of the pore volume from pores with diameters between 1 and 5 micrometers; a pore size distribution between 1 and 5 micrometers, a pore volume from pores with a diameter of 5 micrometers and above less than 0.20 ml/g, and a pore volume from pores with a diameter smaller than 1 micrometer less than 0.20 ml/g, and an effective amount of silver and a promoting amount of rhenium, lithium, cesium, sulfur and tungsten disposed on said carrier.

In yet another aspect of the present invention, a process for the oxidation of an olefin, particularly but not limited to ethylene, to an olefin oxide, particularly but not limited to ethylene oxide, is provided that comprises the vapor phase oxidation of an olefin (e.g., ethylene) with molecular oxygen in a fixed bed, tubular reactor, in the presence of the inventive catalyst described above.

It should be noted that although the inventive catalyst is specifically described and illustrated as a silver-based olefin oxidation catalyst in the present application, the inventive carrier can also be used in other catalytic systems including, for example, a catalyst system wherein the active metal is a metal selected from Group IVB, VB, VIIB, VIIB, VIII, IB and/or JIB of the Periodic Table of Elements; this nomenclature is based on the CAS version of the Periodic Table of Elements.

DETAILED DESCRIPTION OF THE INVENTION

The present invention, which provides a carrier, a catalyst containing the carrier, and a process for producing an olefin oxide using the catalyst, is now described in greater detail.

As stated above, the present invention provides a catalytic system including at least one catalytically active metal disposed thereon comprising a refractory solid carrier having a geometric shape in which at least one wall thickness of said geometric shape is less than 2.5 mm.

The carrier employed in this invention may be prepared or selected from a large number of solid, refractory carriers commercially available. The carriers are relatively inert to the epoxidation feedstock materials, products and reaction conditions for the intended use, such as for the epoxidation of an olefin, for example the oxidation of ethylene to ethylene oxide by the vapor phase oxidation of ethylene with molecular oxygen. The carrier may comprise aluminum oxide such as alpha-alumina, charcoal, pumice, magnesia, zirconia, titania, kieselguhr, fuller's earth, silicon carbide, silica, silicon carbide, silicon dioxide, clays, artificial zeolites, natural zeolites, ceramics and combinations thereof. The preferred carriers are alpha-alumina particles which are often bonded together by a bonding agent and have a very high purity, i.e., about 95% or more, preferably 98 wt. % or more alpha-alumina. Remaining components may be other phases of alumina, silica, alkali metal oxides (e.g., sodium oxide) and trace amounts of other metal-containing and/or non-metal-containing additives or impurities.

A wide variety of such carriers are commercially available. Suitable alumina carriers are manufactured and generally commercially available from Noritake of Nagoya, Japan, and the NorPro Company of Akron, Ohio.

Certain types of alpha alumina-containing carriers are particularly preferred. These alpha alumina carriers are characterized by having a B.E.T. surface area from about 0.3 m$^2$/g to about 3 m$^2$/g, preferably from about 0.6 m$^2$/g to about 2.5 m$^2$/g, more preferably from about 0.9 m$^2$/g to about 2.0 m$^2$/g; and a water pore volume from about 0.10 cc/g to about 0.80 cc/g, preferably from about 0.20 cc/g to about 0.60 cc/g. In a preferred carrier, at least 40% of the pore volume comes from pores with diameters between 1 and 5 micrometers; preferably at least 60%; and most preferably at least 80%. The median pore diameter of the carrier employed in the invention is typically between 1 and 5 micrometers; preferably between 1 and 4.5 micrometers; and most preferably between 1 and 4 micrometers; the pore volume from pores with a diameter of 5 micrometers and above is less than 0.20 ml/g; preferably less than 0.10 ml/g; and most preferably less than 0.05 ml/g. The pore volume from pores with a diameter of 1 micrometer and less is less than 0.20 ml/g; preferably less than 0.16 ml/g; and most preferably less than 0.12 ml/g.

The B.E.T. method for determining specific surface area is described in detail in Brunauer, S., Emmett, P. H. and Teller, E., J. Am. Chem. Soc., 60, 309-16 (1938). Pore volume and the pore size distribution are measured by a conventional mercury porosimeter method; see Drake and Ritter, "Ind. Eng. Chem. Anal. Ed.," 17, 787 (1945).

Regardless of the character of the carrier used, it is usually shaped into geometric shapes such as, for example, pellets, rings, spheres, three-holes, wagon wheels, cross-partitioned hollow cylinders, honeycombs and the like, of a size suitable for employment in fixed bed reactors.

Desirably, the carrier particles may have "equivalent diameters" in the range from about 3 mm to about 10 mm and preferably in the range from about 4 mm to about 9 mm, which are usually compatible with the internal diameter of the tube reactors in which the catalyst is to be placed. "Equivalent diameter" is the diameter of a sphere having the same external surface (i.e., neglecting surface within the pores of the particle) to volume ratio as the carrier particles being employed.

A high catalyst effectiveness is desirable because it results in higher yields of olefin oxide. Catalyst effectiveness is a function of carrier/catalyst shape and thickness and is expressed as an effectiveness factor, $\eta$, that Perry, R. H. and Green, D. W. "Perry's Chemical Engineering Handbook," Sixth Edition, McGraw-Hill, 1984, pg. 4-40 define as:

$$\eta = \frac{\text{actual diffusion-affected reaction rate}}{\text{rate of same reaction without diffusion resistance}}$$

The effectiveness factor is, in turn, an inverse function of a modulus m:

$$m = l\sqrt{\frac{k'(C_{io})^{n-1}}{D_t}}$$

where l is a characteristic length in this case, one half the width of the catalyst wall and the other factors are related to pore geometry, diffusion and kinetics. The greater the length l, the greater the m modulus and the lower the effectiveness factor.

When the carrier is shaped as a hollow cylinder it preferably has thin walls, less than 2.5 mm; more preferably less than 2.0 mm; and most preferably less than 1.5 mm. While it is an important aspect of the invention for the wall thickness to be small, the crush strength should be sufficient for catalyst on the carrier to be loaded into the reactor. As, for example, U.S. Pat. No. 5,380,697 describes the crush strength of the carrier for EO catalyst is at least about 5 pounds.

In general, a suitable catalyst carrier of the present invention can be prepared by mixing the refractory material, such as alumina, a solvent such as water, a temporary binder or burnout material, a permanent binder and/or a porosity controlling agent. Temporary binders, or burnout materials, include cellulose, substituted celluloses, e.g., methylcellulose, ethylcellulose, and carboxyethylcellulose, stearates, such as organic stearate esters, e.g., methyl or ethyl stearate, waxes, granulated polyolefins, particularly polyethylene and polypropylene, walnut shell flour, and the like which are decomposable at the temperatures employed. The binders are responsible for producing the porosity of the carrier material. Burnout material is used primarily to ensure the preservation of a porous structure during the green, or unfired phase in which the mixture may be shaped into particles by molding or extrusion processes. It is essentially totally removed during the firing to produce the finished carrier. The carriers of the invention are preferably made with the inclusion of a bond material such as silica with an alkali metal compound in sufficient amount to substantially prevent the formation of crystalline silica compounds. Permanent binders include, for example, inorganic clay-type materials. A convenient binder material which may be incorporated with the alumina particles is a mixture of boehmite, an ammonia stabilized silica sol and a soluble sodium salt. The formed paste is extruded or molded into the desired shape and fired at a temperature of from about 1200° C. to about 1600° C. to form the carrier. Where the particles are formed by extrusion, it may be desirable to include conventional extrusion aids. The amounts of the components to be used are to some extent interdependent and will depend on a number of factors that relate to the equipment used. However these matters are well within the general knowledge of a person skilled in the art of extruding ceramic materials. The performance of the carrier is enhanced if it is treated by soaking the carrier in a solution of an alkali hydroxide such as sodium hydroxide, potassium hydroxide, or an acid such as HNO$_3$ as described in U.S. Patent Application Publication No. 2006/0252643 A1. After treatment, the carrier is preferably washed, such as with water, to remove unreacted dissolved material and treating solution and optionally dried.

In order to produce a catalyst for the oxidation of an olefin to an olefin oxide, a carrier having the above characteristics is then provided with a catalytically effective amount of silver thereon. The catalysts are prepared by impregnating the carriers with silver ions, compounds, complexes and/or salts dissolved in a suitable solvent sufficient to cause deposition of silver precursor compound onto the carrier. The impregnated carrier is then removed from the solution and the deposited silver compound is reduced to metallic silver by high temperature calcination.

Also preferably deposited on the carrier either prior to, coincidentally with, or subsequent to the deposition of the silver are suitable promoters in the form of ions, compounds and/or salts of an alkali metal dissolved in a suitable solvent.

Also deposited on the carrier either prior to, coincidentally with, or subsequent to the deposition of the silver and/or alkali metal are suitable transition metal ions, compounds, complexes and/or salts dissolved in an appropriate solvent.

The original or treated carrier as described above is impregnated with a silver impregnating solution, preferably an aqueous silver solution. The carrier is also impregnated at the same time or in a separate step with various catalyst promoters. Preferred catalysts prepared in accordance with this invention contain up to about 45% by weight of silver, expressed as metal, deposited upon the surface and throughout the pores of a porous refractory carrier. Silver contents, expressed as metal, of from about 1 to about 40% based on weight of total catalyst are preferred, while silver contents of from about 8 to about 35% are more preferred. The amount of silver deposited on the support or present on the carrier is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide and selectivity and activity stability within catalyst life. Useful silver containing compounds non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

This catalyst comprises a catalytically effective amount of silver, a promoting amount of alkali metal, a promoting amount of a transition metal supported on a porous, refractory carrier. As used herein the term "promoting amount" of a certain component of a catalyst refers to an amount of that component that works effectively to provide an improvement in one or more of the catalytic properties of that catalyst when compared to a catalyst not containing said component. The exact concentrations employed, of course, will depend upon, among other factors, the desired silver content, the nature of the carrier, the viscosity of the liquid, and solubility of the silver compound.

In addition to silver, the catalyst may also contain an alkali metal promoter selected from lithium, sodium, potassium, rubidium, cesium or combinations thereof, with, cesium being preferred. The amount of alkali metal deposited on the carrier or catalyst or present on the carrier or catalyst is to be a promoting amount. Preferably the amount will range from about 10 ppm to about 3000 ppm, more preferably from about 15 ppm to about 2000 ppm and even more preferably from about 20 ppm to about 1500 ppm and yet even more preferably from about 50 ppm to about 1000 ppm by weight of the total catalyst, measured as the metal.

The catalyst may also preferably contain a transition metal promoter which comprises an element from Groups VB, VIIB, VIIB and VIII of the Periodic Table of the Elements, and combinations thereof. Preferably the transition metal comprises an element selected from Group VIIB of the Periodic Table of the Elements. More preferred transition metals are rhenium, molybdenum, and tungsten, with molybdenum and rhenium most preferred. The amount of transition metal promoter deposited on the carrier or catalyst or present on the carrier or catalyst is to be a promoting amount. The transition metal promoter may be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur components, one or more fluorine containing components, or combinations thereof.

The silver solution used to impregnate the carrier may also comprise an optional solvent or complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles of ethylene diamine per mole of silver, preferably from about 0.2 to about 4.0 moles, and more preferably from about 0.3 to about 3.0 moles of ethylene diamine for each mole of silver.

When a solvent is used it may be water-based, or organic-based, and may be polar or substantially or totally non-polar. In general, the solvent should have sufficient solvating power to solubilize the solution components. At the same time, it is preferred that the solvent be chosen to avoid having an undue influence on or interaction with the solvated promoters. Examples of organic-based solvents include, but are not limited to, alcohols, in particular alkanols; glycols, in particular alkyl glycols; ketones; aldehydes; amines; tetrahydrofuran; nitrobenzene; nitrotoluene and the like. Organic-based solvents that have 1 to about 8 carbon atoms per molecule are preferred. Mixtures of organic solvents or of water and one or more organic solvents may be used, provided that such mixed solvents function as desired herein.

The concentration of silver salt in the solution is in the range from about 0.1% by weight to the maximum permitted by the solubility of the particular salt/solubilizing agent combination employed. It is generally very suitable to employ silver salts solutions containing from 0.5% to about 45% by weight of silver with silver salt concentrations from 5 to 30% by weight being preferred.

Impregnation of the selected carrier is achieved in conventional manners by excess solution impregnation, incipient wetness, etc. Typically, the carrier material is placed in the silver solution until a sufficient amount of the solution is absorbed by the carrier. Preferably the quantity of the silver solution used to impregnate the porous carrier is no more than is necessary to fill the pore volume of the carrier. The silver containing liquid penetrates by absorption, capillary action and/or vacuum into the pores of the carrier. A single impregnation or a series of impregnations, with or without intermediate drying, may be used, depending in part on the concentration of the silver salt in the solution. Impregnation procedures are described in U.S. Pat. Nos. 4,761,394, 4,766, 105, 4,908,343, 5,057,481, 5,187,140, 5,102,848, 5,011,807, 5,099,041 and 5,407,888, which are incorporated herein by reference. Known prior procedures of pre-deposition, co-deposition and post-deposition of various the promoters can also be employed.

Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is her understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to optimize conditions and results by taking into account feedstock costs, energy costs, by-product removal costs and the like. The particular combination of silver, carrier, alkali metal promoter, and transition metal promoter of the instant invention will provide an improvement in one or more catalytic properties over the same combination of silver and carrier and none, or only one promoter.

After impregnation, the carrier impregnated with silver precursor compound and the promoters is calcined or activated, for a time sufficient to reduce the silver component to metallic silver and to remove volatile decomposition products from the silver containing support. The calcination is accomplished by heating the impregnated carrier, preferably at a gradual rate, to a temperature in the range from about 200° C. to about 600° C., preferably from about 250° C. to about 500° C., and more preferably from about 300° C. to about 450° C., at a reaction pressure in the range from about 0.5 to about 35 bar, for a time sufficient to convert the contained silver to silver metal and to decompose all or substantially all of present organic materials and remove the same as volatiles. In general, the higher the temperature, the shorter the required reduction period. A wide range of heating periods have been suggested in the art to thermally treat the impregnated support, (e.g., U.S. Pat. No. 3,563,914 suggests heating for less than 300 seconds, U.S. Pat. No. 3,702,259 discloses heating from 2 to 8 hours at a temperature of from 100° C. to 375° C. to reduce the silver salt in the catalyst; usually for from about 0.5 to about 8 hours, however, it is only important that the reduction time be correlated with temperature such that substantially complete reduction of silver salt to catalytically active metal is accomplished). A continuous or step-wise heating program may be used for this purpose.

After preparing the silver catalyst using the procedures mentioned above, the catalyst is used for the production of ethylene oxide. Generally, the commercially practiced ethylene oxide production processes are carried out by continuously contacting an oxygen containing gas with ethylene in the presence of the present catalysts at a temperature in the range from about 180° C. to about 330° C. and preferably about 200° C. to about 325° C., more preferably from about 225° C. to about 270° C., at a pressure which may vary from about atmospheric pressure to about 30 atmospheres depending on the mass velocity and productivity desired. Pressures in the range of from about atmospheric to about 500 psi are generally employed. Higher pressures may, however, be employed within the scope of the invention. Residence times in large-scale reactors are generally on the order of about 0.1 to about 5 seconds. Oxygen may be supplied to the reaction as pure oxygen or in an oxygen containing stream, such as air. The resulting ethylene oxide is separated and recovered from the reaction products using conventional methods. However, for this invention, the ethylene oxide process envisions the normal gas recycle encompassing carbon dioxide recycle in the normal concentrations, e.g., about 0.5 to about 6 volume percent. A usual process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst.

The inventive catalysts have been shown to be particularly selective catalysts in the oxidation of ethylene with molecular oxygen to ethylene oxide. The conditions for carrying out such an oxidation reaction in the presence of the catalyst of the present invention broadly comprise those described in the prior art. This applies, for example, to suitable temperatures, pressures, residence times, diluent materials such as nitrogen, carbon dioxide, steam, argon, methane or other saturated hydrocarbons, the presence or absence of moderating agents to control the catalytic action, for example, 1,2-dichloroethane, vinyl chloride or ethyl chloride, the desirability of employing recycle operations or applying successive conversion in different reactors to increase the yields of ethylene oxide, and any other special conditions which may be selected in processes for preparing ethylene oxide. Molecular oxygen employed as a reactant may be obtained from conventional sources. The suitable oxygen charge may be relatively pure oxygen, a concentrated oxygen stream comprising oxygen in major amount with lesser amounts of one or more diluents such as nitrogen, argon, etc., or another oxygen containing stream such as air. The use of the inventive catalyst in ethylene oxidation reactions is in no way limited to the use of specific conditions among those which are known to be effective.

The resulting ethylene oxide is separated and recovered from the reaction products by conventional methods known and used in the art. Use of the silver catalyst of the invention in ethylene oxide production processes gives higher overall ethylene oxidation selectivities to ethylene oxide at a given ethylene conversion than are possible with conventional catalysts.

In the production of ethylene oxide, reactant feed mixtures may contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene usually is reacted per pass over the catalyst and after separation of the desired ethylene oxide product and the removal of an appropriate purge stream and carbon dioxide to prevent uncontrolled build up of inert products and/or by-products, unreacted materials are returned to the oxidation reactor. For purposes of illustration only, the following are conditions that are often used in current commercial ethylene oxide reactor units. GHSV—1500-10,000; inlet pressure—150-400 psig; inlet feed: ethylene—1-40%; $O_2$—3-12%; $CO_2$—0.5-40%; ethane 0-3%; 0.3-20 ppmv total diluent chlorohydrocarbon moderator; balance argon and/or methane and/or nitrogen, coolant temperature—180-315° C.; $O_2$ conversion level—10-60%; EO Production (Work Rate) 100-300 kg EO/hr/cu meters catalyst.

In other descriptions of processes of ethylene oxide production addition of oxygen-containing gases to the feed increased the efficiency. For example, U.S. Pat. No. 5,112,795 discloses an addition of 5 ppm of nitric oxide to a gas feed having the following general composition: 8 volume % oxygen, 30 volume % ethylene, about 5 ppmw ethyl chloride and the balance nitrogen.

The following non-limiting example serves to illustrate the invention.

EXAMPLE

Catalysts Preparation and Testing

1. Silver Stock Solution Preparation.

A silver solution was prepared using the following components (parts are by weight unless otherwise noted):
 1. Silver oxide—834 parts
 2. Oxalic acid—444 parts
 3. Ethylene diamine—566 parts
 4. Deionized water—744 parts At stirring, ethylene diamine was added to water first followed by oxalic acid addition. Temperature during these additions was maintained below 50° C. After each addition the solution was cooled down to 20° C. before next addition step. Finally, silver oxide was added at a temperature maintained below 42° C. Final solution was cooled down to 30° C. before filtering. The clear filtrate was utilized as a silver/amine stock solution for catalyst preparation.

2. Catalyst Preparation and Testing.

a. Carriers.

Carriers A and B used for comparison study are in Table I. Each carrier was treated with 0.025 M NaOH solutions at 80° C. for 1.5 hour followed by three deionized water rinse steps at ambient temperature to remove NaOH. Weight ratio between carrier and solutions was kept as 1/1.3. After treatment the carriers were dried at 150° C.

b. Promoter Addition.

Cesium hydroxide was added to the solution above in order to prepare a catalyst containing catalytically effective amounts of silver and cesium.

c. Carrier Impregnation.

40 kg of carrier A were placed in a stainless steel vessel for impregnation. 3.1 kg of comparison carrier B were placed in a glass vessel. The impregnation vessel in each case was then exposed to vacuum until the pressure was below 50 mm Hg. Silver/promoter solution was introduced to the flask while it was still under vacuum in the amount to fully cover the carrier. The pressure of the vessel was allowed to rise to atmospheric pressure. The catalyst was separated from the solution and was ready for calcination.

d. Catalyst Calcination.

Calcination, i.e., the deposition of metallic silver, was induced by heating the catalyst up to the decomposition temperature of the silver salt. This was achieved via heating in a furnace that has several heating zones in a controlled atmosphere. The catalyst was loaded on a moving belt that entered the furnace at ambient temperature. The temperature was gradually increased as the catalyst passed from one zone to the next. The temperature was increased, up to 400° C. in the hottest zone. After the heating zones, the belt passed through a cooling zone that gradually cooled the catalyst to ambient temperature. The atmosphere in the furnace was controlled through the use of nitrogen flow in the heating zones.

e. Catalyst Testing.

The test results are in Table I. 3.20 kg of catalyst made on carrier A, and 2.43 kg of catalyst made on carrier B were charged and tested in the same reactor under the same reaction conditions at a Volumetric Work Rate equal to 160÷180 kg EO per hour per cubic meter of catalyst.

Table I demonstrates higher effectiveness of catalyst on carrier B. Catalyst made on a carrier with thin walls requires less of a catalyst loading, works at a lower pressure drop, and exhibits higher selectivity than catalysts made on a carrier with thicker walls and higher loadings.

TABLE I

Carriers and catalysts comparison.

| Catalyst | Nominal Outside Diameter, mm | Wall Thickness, mm | Catalyst Loading, kg/m$^3$ | Pressure Drop, psi | Selectivity, % | Temp., ° C. |
|---|---|---|---|---|---|---|
| A | 8.3 | 2.75 | 754 | 11.1 | 81.7 | 217 |
| B | 8.3 | 1.3 | 597 | 5.8 | 82.8 | 219 |

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A carrier for a catalytic system having at least one catalytically active metal disposed thereon comprising:
 a geometrically shaped refractory solid carrier in which at least one wall thickness of said geometrically shaped refractory solid carrier is less than 2.5 mm, wherein said geometrically shaped refractory solid carrier is in a form selected from a pellet, a ring, a sphere, a wagon wheel, a cross-partitioned hollow cylinder and a honeycomb, and wherein said geometrically shaped refractory solid carrier has a total pore volume from about 0.2 ml/g to about 0.6 ml/g with at least 40% of the pore volume from pores with diameters between 1 and 5 micrometers.

2. The carrier of claim 1 wherein said at least one wall thickness is less than 2.0 mm.

3. The carrier of claim 1 wherein said at least one wall thickness is less than 1.5 mm.

4. The carrier of claim 1 wherein the geometrically shaped refractory solid carrier comprises aluminum oxide, charcoal, pumice, magnesia, zirconia, titania, kieselguhr, fuller's earth, silicon carbide, silica, clays, artificial zeolites, natural zeolites, ceramics or combinations thereof.

5. The carrier of claim 1 wherein said geometrically shaped refractory solid carrier is aluminum oxide having a purity of about 90% or more.

6. The carrier of claim 1 wherein said geometrically shaped refractory solid carrier further includes at least one of the following characteristics: (i) a surface area from about 0.3 to about 3.0 m$^2$/g; (ii) a pore size distribution between 1 and 5 micrometers; (iii) a pore volume from pores with a diameter of 5 micrometers and above less than 0.20 ml/g; and (iv) a pore volume from pores with a diameter smaller than 1 micrometer less than 0.20 ml/g.

7. A carrier for a catalytic system having at least one catalytically active metal disposed thereon comprising:
   a geometrically shaped refractory solid carrier in which at least one wall thickness of said geometrically shaped refractory solid carrier is less than 2.5 mm, said carrier comprises aluminum oxide having a total pore volume from about 0.2 ml/g to about 0.6 ml/g, a surface area from about 0.3 to about 3.0 m$^2$/g, at least 40% of the pore volume from pores with diameters between 1 and 5 micrometers, a pore size distribution between 1 and 5 micrometers, a pore volume from pores with a diameter of 5 micrometers and above less than 0.20 ml/g, and a pore volume from pores with a diameter smaller than 1 micrometer less than 0.20 ml/g.

8. A catalyst useful for the epoxidation of an olefin comprising:
   a geometrically shaped refractory solid carrier in which at least one wall thickness of said carrier is less than 2.5 nm, wherein said geometrically shaped refractory solid carrier is in a form selected from a pellet, a ring, a sphere, a wagon wheel, a cross-partitioned hollow cylinder and a honeycomb, and wherein said geometrically shaped refractory solid carrier has a total pore volume from about 0.2 ml/g to about 0.6 ml/g with at least 40% of the pore volume from pores with diameters between 1 and 5 micrometers; and a catalytically effective amount of silver disposed thereon.

9. The catalyst of claim 8 wherein said at least one wall thickness is less than 2.0 mm.

10. The catalyst of claim 8 wherein said at least one wall thickness is less than 1.5 mm.

11. The catalyst of claim 8 wherein the geometrically shaped refractory solid carrier comprises aluminum oxide, charcoal, pumice, magnesia, zirconia, titania, kieselguhr, fuller's earth, silicon carbide, silica, clays, artificial zeolites, natural zeolites, ceramics or combinations thereof.

12. The catalyst of claim 8 wherein said geometrically shaped refractory solid carrier is aluminum oxide having a purity of about 90% or more.

13. The catalyst of claim 8 wherein said geometrically shaped refractory solid carrier further includes at least one of the following characteristics: (i) a surface area from about 0.3 to about 3.0 m$^2$/g; (ii) a pore size distribution between 1 and 5 micrometers; (iii) a pore volume from pores with a diameter of 5 micrometers and above less than 0.20 ml/g; and (iv) a pore volume from pores with a diameter smaller than 1 micrometer less than 0.20 ml/g.

14. The catalyst of claim 8 further comprising a promoting amount of a promoter thereon, the promoter comprising one or more of an alkali metal containing compounds, one or more transition metal containing compounds, one or more sulfur components, one or more fluorine containing components, or combinations thereof.

15. The catalyst of claim 14 wherein the promoter is a transition metal comprising at least one element selected from the group consisting of Groups VB, VIB, VIIB and VIII of the Periodic Table of the Elements.

16. The catalyst of claim 14 wherein the transition metal comprises rhenium, molybdenum, tungsten or combinations thereof.

17. The catalyst of claim 14 wherein the promoter is an alkali metal containing compound comprising lithium, sodium, potassium, rubidium, cesium or combinations thereof.

18. The catalyst of claim 8 further comprises a promoting amount of rhenium, lithium, cesium, sulfur and optional tungsten disposed on said carrier.

19. A catalyst useful for the epoxidation of an olefin comprising:
   a geometrically shaped refractory solid carrier in which at least one wall thickness of said geometrically shaped refractory solid carrier is less than 2.5 mm, said carrier comprises aluminum oxide having a total pore volume from about 0.2 ml/g to about 0.6 ml/g, a surface area from about 0.3 to about 3.0 m$^2$/g, at least 40% of the pore volume from pores with diameters between 1 and 5 micrometers, a pore size distribution between 1 and 5 micrometers, a pore volume from pores with a diameter of 5 micrometers and above less than 0.20 ml/g, and a pore volume from pores with a diameter smaller than 1 micrometer less than 0.20 ml/g; and an effective amount of silver and a promoting amount of rhenium, lithium, cesium, sulfur and tungsten disposed on said carrier.

20. A carrier for a catalytic system having at least one catalytically active metal disposed thereon comprising:
   a geometrically shaped refractory solid carrier in which at least one wall thickness of said geometrically shaped refractory solid carrier is less than 2.5 mm, wherein said geometrically shaped refractory solid carrier is in a form selected from a pellet, a ring, a sphere, a wagon wheel, a cross-partitioned hollow cylinder and a honeycomb, and wherein said carrier has a pore volume from pores with a diameter of 5 micrometers and above of less than 0.20 ml/g.

21. A carrier for a catalytic system having at least one catalytically active metal disposed thereon comprising:
   a geometrically shaped refractory solid carrier in which at least one wall thickness of said geometrically shaped refractory solid carrier is less than 2.5 mm, wherein said geometrically shaped refractory solid carrier is in a form selected from a pellet, a ring, a sphere, a wagon wheel, a cross-partitioned hollow cylinder and a honeycomb, and wherein said carrier has a pore volume from pores with a diameter smaller than 1 micrometer of less than 0.20 ml/g.

22. A catalyst useful for the epoxidation of an olefin comprising:
   a geometrically shaped refractory solid carrier in which at least one wall thickness of said carrier is less than 2.5 nm, wherein said geometrically shaped refractory solid carrier is in a form selected from a pellet, a ring, a sphere, a wagon wheel, a cross-partitioned hollow cylinder and a honeycomb, and wherein said carrier has a pore volume from pores with a diameter of 5 micrometers and above of less than 0.20 ml/g; and a catalytically effective amount of silver disposed thereon.

23. A catalyst useful for the epoxidation of an olefin comprising:
   a geometrically shaped refractory solid carrier in which at least one wall thickness of said carrier is less than 2.5 nm, wherein said geometrically shaped refractory solid carrier is in a form selected from a pellet, a ring, a sphere, a wagon wheel, a cross-partitioned hollow cylinder and a honeycomb, and wherein said carrier has a pore volume from pores with a diameter smaller than 1 micrometer of less than 0.20 ml/g; and a catalytically effective amount of silver disposed thereon.

* * * * *